US012336934B2

United States Patent
Li et al.

(10) Patent No.: US 12,336,934 B2
(45) Date of Patent: Jun. 24, 2025

(54) SELF-SEALING TRABECULECTOMY

(71) Applicant: THE EYE HOSPITAL OF WENZHOU MEDICAL UNIVERSITY, Wenzhou (CN)

(72) Inventors: Guoxing Li, Wenzhou (CN); Rongrong Le, Wenzhou (CN); Yuanbo Liang, Wenzhou (CN); Shaodan Zhang, Wenzhou (CN); Yanqian Xie, Wenzhou (CN); Aiwu Fang, Wenzhou (CN)

(73) Assignee: THE EYE HOSPITAL OF WENZHOU MEDICAL UNIVERSITY, Wenzhou (CN)

( * ) Notice: Subject to any disclaimer, the term of this patent is extended or adjusted under 35 U.S.C. 154(b) by 408 days.

(21) Appl. No.: 18/165,664

(22) Filed: Feb. 7, 2023

(65) Prior Publication Data

US 2024/0261143 A1  Aug. 8, 2024

(51) Int. Cl.
*A61F 9/007* (2006.01)
*A61F 9/008* (2006.01)

(52) U.S. Cl.
CPC .......... *A61F 9/007* (2013.01); *A61F 9/00781* (2013.01); *A61F 2009/00891* (2013.01)

(58) Field of Classification Search
CPC ................ A61F 9/00781; A61F 9/007; A61F 2009/00891
See application file for complete search history.

(56) References Cited

U.S. PATENT DOCUMENTS 5,370,641 A * 12/1994 O'Donnell, Jr. ........ A61F 9/008
606/4

FOREIGN PATENT DOCUMENTS

CN 219423256 U * 7/2023

OTHER PUBLICATIONS

Translation of CN219423256U (Year: 2023).*

* cited by examiner

*Primary Examiner* — Leslie R Deak
(74) *Attorney, Agent, or Firm* — Christensen, Fonder, Dardi & Herbert PLLC; John P. Fonder

(57) ABSTRACT

A self-sealing trabeculectomy, which solves the problems in existing scleral flap suturing. The self-sealing trabeculectomy includes the following steps: S1: before a surgery, conducting disinfection, draping and eye speculum placement, and conducting local infiltration anesthesia under a surgical eye conjunctiva; S2: making a conjunctival flap; S3: making a 4 mm×3 mm or 4 mm×4 mm scleral flap; S4: resecting a root of an iris and trabecular tissues, smoothing the scleral flap with a restoration instrument, and suturing the bulbar conjunctiva with a nylon thread to reach a watertight state; S5: removing a suspending suture for the rectus or a cornea, reducing the eye speculum to weaken a tension of the eye speculum, and forming an anterior chamber; S6: taking out the eye speculum; and S7: after the surgery, conventionally locally applying a corticosteroid hormone and a non-steroid anti-inflammatory drug, keeping a filtration channel unobstructed.

9 Claims, 5 Drawing Sheets

SELF-SEALING TRABECULECTOMY

FIELD OF THE INVENTION

The present invention relates to a novel self-sealing trabeculectomy.

BACKGROUND OF THE INVENTION

Glaucoma may cause irreversible visual loss and is the second leading cause of blindness, next to a cataract. There were 80 million persons with glaucoma in the world by 2020, and it is expected to reach 141 million persons with glaucoma by 2040, wherein persons with glaucoma in Asia account for about 60%. In addition, as glaucoma is latent, about 50% of patients living in less-developed areas are not effectively diagnosed and treated. Research shows that there are more than 2 million persons in America that have glaucoma with a blindness rate of 11% and about 120 thousand persons losing their sight; with the treatment cost reaching up to about 1.5 billion dollars each year. As the global population ages, the incidence and the burden of glaucoma are expected to significantly increase. In addition, this data does not include the huge amount of patients with secondary glaucoma. Therefore, the situation of research on prevention and treatment of glaucoma is extremely serious.

At present, treatment of glaucoma mainly comprises drug treatment, laser treatment and surgical treatment. In recent years, clinical application of a new drug (such as prostaglandin) for treating glaucoma rescues and slows visual functions of many patients with glaucoma, particularly, open-angle glaucoma, and improves the quality of life of the patients. Ocular surface administration, such as eye drops, has the side effect of increasing eyelash length, conjunctival congestion, permanent blackening of the iris, reduction in periorbital fats and the like, which limits clinical applications of this type of drug. In addition, complexity of an administration combined mode and long-term application of the drugs both bring challenges to the compliance and the tolerance of the patients. Laser treatment has a certain function as an auxiliary means for initial treatment and drug treatment for glaucoma, but often requires to be conducted many times, and has limited effect on patients with late-stage glaucoma; and the long-term effect of laser treatment requires further research. A minimally-invasive glaucoma surgery (MIGS) arising in recent years has had great success; however, MIGS is generally used for treating early glaucoma, and the long-term effect of MIGS, serving as a transition treatment method for the drug treatment and invasive trabeculectomy, requires to be further proved.

Traditional compound trabeculectomy is still a golden standard for glaucoma surgical treatment at present due to large antihypertensive amplitude and lasting effects. Late cases and failure cases undergoing drugs, laser light and minimally invasive surgery for glaucoma still require treatment with trabeculectomy. Research show that trabeculectomy may effectively reduce a progression of visual field deterioration of glaucoma. The basic principle is that the effect of lowering an intraocular pressure to treat glaucoma is achieved by forming a filtering bleb functioning for a long term on the surface of an eyeball through the surgery, where scleral flap suturing is a key step for the surgery and is also a main reason causing postsurgical complications and surgery failures; if it is loose in suturing, an anterior chamber is shallow or disappears in the early stage after the surgery, which results in too low of an intraocular pressure; and if it is too tight in suturing, the intraocular pressure is high after the surgery, and the scleral flap would be closed without timely treatment, which increases the failure rate of the surgery. An adjustable suture plays a certain role in increasing the success rate of the surgery. However, removal of the adjustable suture may cause a secondary damage; and meanwhile, the removing time is difficult to grasp, filtration is too strong if removal is too early, and the suture effect is in failure due to scarring if removal is too late. Other researchers believe that a scleral flap suture, as a foreign matter, natively is one of the causes of scarring of a filtration channel after the surgery. Previous other researchers discover that excessive scleral flap suturing in the surgery may produce large corneal astigmatism even exceeding 10 D or above, which severely affects the visual quality of the patient after the surgery.

SUMMARY OF THE INVENTION

In order to solve the problems in existing trabeculectomy, the present invention provides a novel self-sealing trabeculectomy mainly used for treating various kinds of glaucoma. Through technical improvements, the present invention removes a step of sclera suturing in traditional trabeculectomy, so as to fulfill an automatic filtering and adjusting function of a scleral flap and greatly improve the safety of a surgery.

The technical solution of the present invention is as follows: novel self-sealing trabeculectomy comprises the surgical steps:

S1: before a surgery, conventionally conducting disinfection, draping and eye speculum placement, diluting an iodophor solution for irrigating a conjunctival sac, and conducting local infiltration anesthesia under a surgical eye conjunctiva with 0.4 ml of 2% lidocaine;

S2: conducting traction suturing on a superior rectus or a corneal limbus, then fixing a superior corneoscleral limbus with suturing, annularly incising a bulbar conjunctiva at an edge from a 11 o'clock position to a 1 o'clock position, and making a conjunctival flap with a corneoscleral limbus or a fornix as a base by taking 12 o'clock position as a center;

S3: making a 4 mm×3 mm or 4 mm×4 mm scleral flap with a thickness of ½-⅔ of that of a sclera, and using the scleral flap with or without an antimetabolite;

S4: conventionally resecting a root of an iris and trabecular tissues, smoothing the scleral flap with a restoration instrument, and suturing the bulbar conjunctiva with a nylon thread to reach a watertight state;

S5: removing a suspending suture of the traction suturing of S2 for the rectus or removing a suspending suture for a cornea, reducing the eye speculum to weaken a tension of the eye speculum, telling a patient to relax, and forming an anterior chamber with normal saline or an anterior chamber irrigating solution;

S6: taking out the eye speculum; and

S7: after the surgery, conventionally locally applying a corticosteroid hormone and a non-steroid anti-inflammatory drug; if there is high intraocular pressure in an early stage after the surgery, not massaging an eyeball, and additionally using an anti-glaucoma drug first; if necessary, slightly pressing the edge of the scleral flap at Day 3 after the surgery, and gently opening the fully closed scleral flap; and at Day 7 after the surgery, conducting normal eyeball massage to lower an intraocular pressure and keep a filtration channel unobstructed.

As a further improvement of the present invention, in step S3, the 4 mm×3 mm or 4 mm×4 mm scleral flap is made using a diamond knife with scales.

As a further improvement of the present invention, in step S3, the scleral flap is in a step shape and is gradually thickened from the position away from the corneal limbus to the corneal limbus; and a thickness of the base of the scleral flap is necessary to be larger than ⅔ or above of a sclera.

As a further improvement of the present invention, in step S4, the restoration instrument used is an iris restorer; and a 10-0 nylon thread is used for suturing the bulbar conjunctiva with 2 stitches, so as to achieve the watertight state.

As a further improvement of the present invention, in step S5, if the anterior chamber is difficult to form, a conjunctival surface with the filtering bleb may be slightly pressed using the iris restorer, and the scleral flap is smoothed, so as to assist formation of the anterior chamber.

As a further improvement of the present invention, in step S6, for a part of patients still with poor formation of the anterior chambers, a filtering function adjusting device is jointly placed in, and an antibiotic eye ointment is coated to finish the surgery.

As a further improvement of the present invention, the filtering function adjusting device is a striped membrane made by silica gel, is in an approximate fan shape, has certain elasticity and plasticity and is closely adhered to the surface of the eyeball.

The filtering function adjusting device is placed at an upper fornix, and a pressure is applied to the scleral flap by an own pressure and a force of an upper eyelid, so as to limit an outer filtering function of the scleral flap.

As a further improvement of the present invention, the filtering function adjusting device may be removed or continuously worn at Day 3 after the surgery if necessary, and may be safely removed at Days 7-10 after the surgery generally.

The present invention has the beneficial effects that the self-sealing trabeculectomy breaks through the law thinking that "the scleral flap requires to be sutured" of the trabeculectomy for the first time, achieves the characteristic of free suturing of the sclera through an improvement on the surgical technology and, compared with traditional trabeculectomy, has the following advantages that: 1. due to the self-sealing scleral flap, occurrence of postsurgical high and low intraocular pressure due to too tight and too loose sutures of the scleral flap is eliminated; and meanwhile, as the filtration channel of the scleral flap after the surgery is continuously unobstructed, the possibility of closure scars of the scleral flap is greatly lowered, and the success rate of the surgery is increased. 2. After the surgery, the steps of laser suture lysis, adjusting suture removal and the like are not required, so that pain of the patient is reduced, and the maintenance process for the filtering bleb after the surgery is simplified. 3. Without stimulation with the suture under the scleral flap, scarring of the scleral flap after the trabeculectomy is further lowered, and the success rate of an anti-glaucoma surgery is increased. 4. Surgically induced astigmatism caused by looseness and tightness of the sclera suture after the surgery is reduced or eliminated, and the visual quality of the patient after the surgery is improved. 5. The surgical steps are simplified, the surgery time is shortened, and the tolerance and postsurgical recovery of the patient are better facilitated. 6. In combination with the trabecula filtering function adjusting device, occurrence of too strong early filtration after the surgery may be avoided, and then the safety of the surgery is greatly improved.

1. Conjunctiva; 2. superior rectus; 3. corneal limbus; 4. conjunctival flap; 5. scleral flap; 6. iris; 7. trabecular tissue; 8. nylon thread; 9. anterior chamber; 10. conjunctival surface with filtering bleb; 11. filtering function adjusting device; 12. upper fornix; 13. traction suturing; 14. unobstruction of filtration channel; 15. bulged filtering bleb.

DETAILED DESCRIPTION OF THE INVENTION

The embodiments of the present invention are further described in combination with the drawings below.

Figure 1:
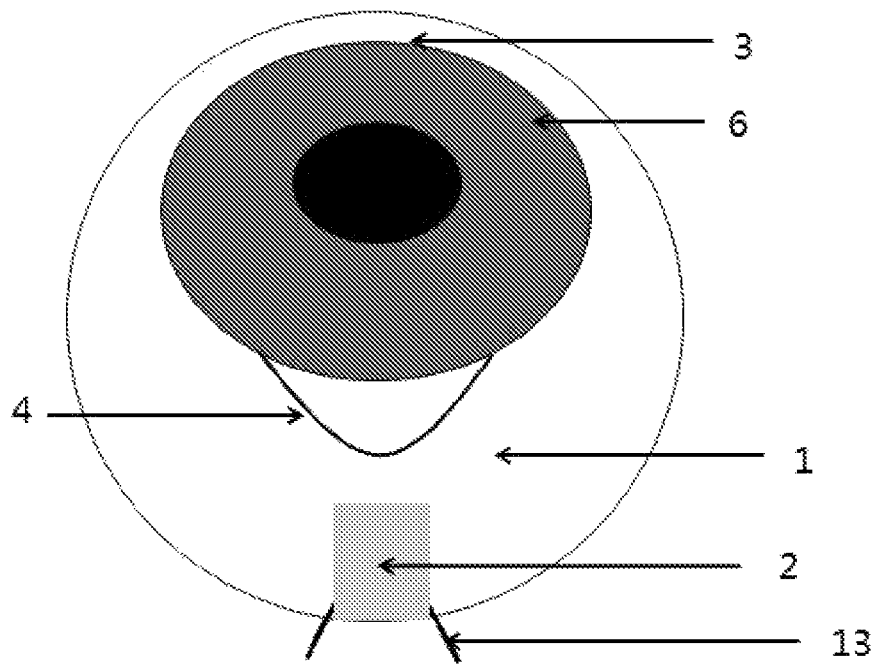
FIG. 1 is a schematic diagram of fixing superior rectus with suturing.
Figure 2:
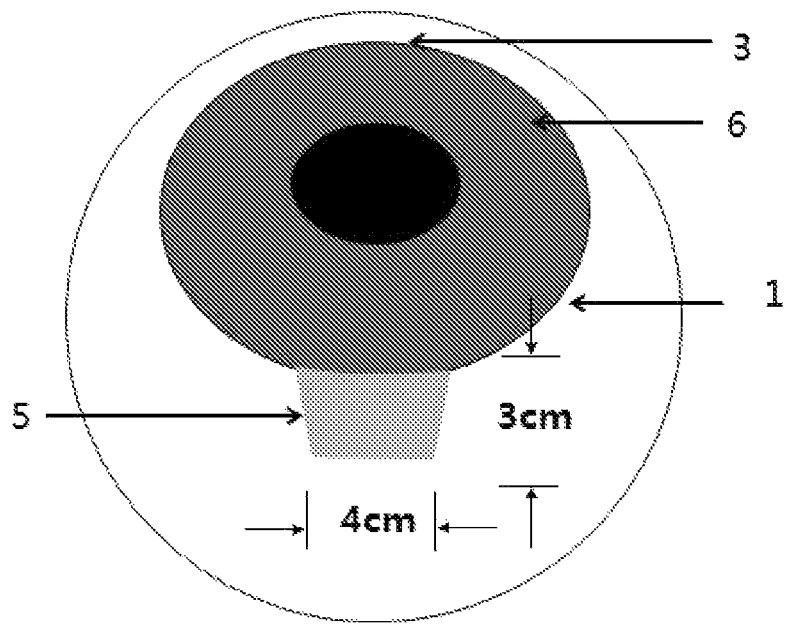
FIG. 2 is a schematic diagram of making a 4 mm×3 mm scleral flap in a surgery.
Figure 3:
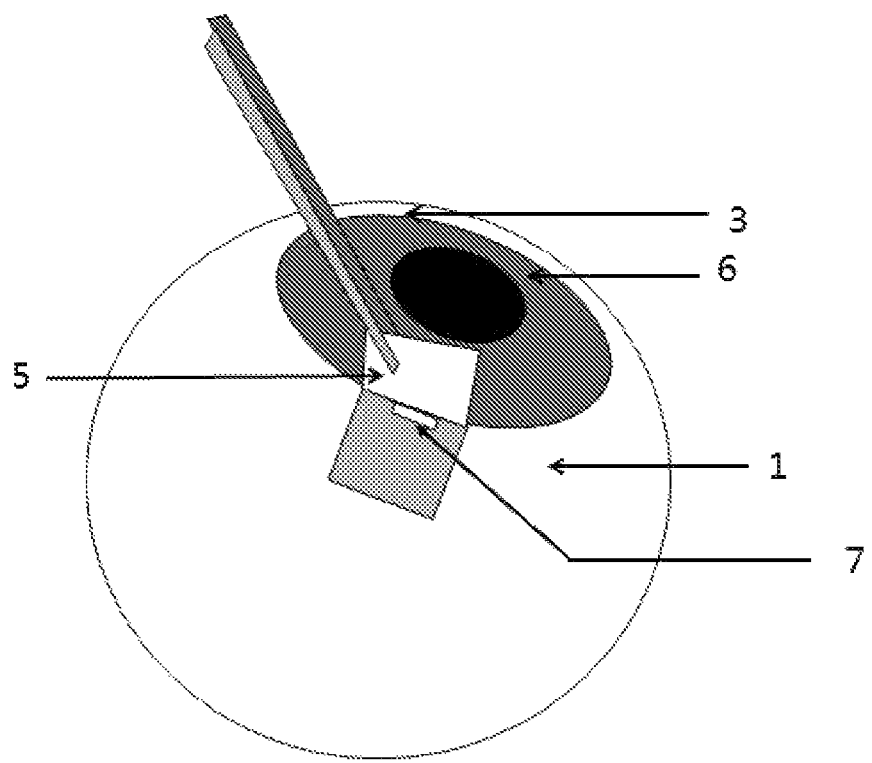
FIG. 3 is a schematic diagram during conventional trabeculectomy.
Figure 4:
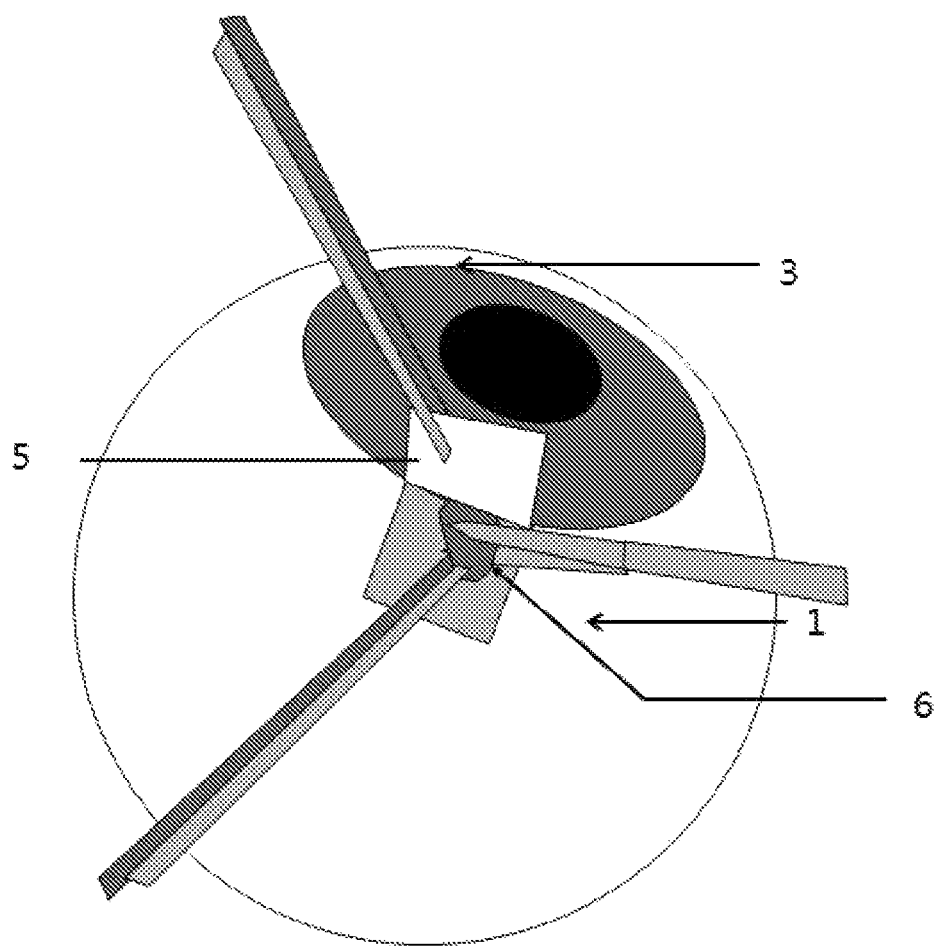
FIG. 4 is a schematic diagram during conventional peripheral iridotomy.
Figure 5:
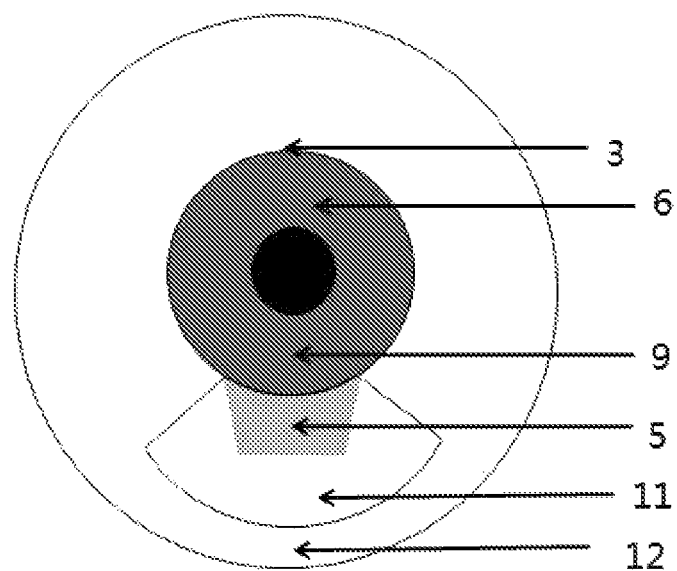
FIG. 5 is a schematic diagram of good formation of an anterior chamber under the condition without suturing a sclera.
Figure 6:
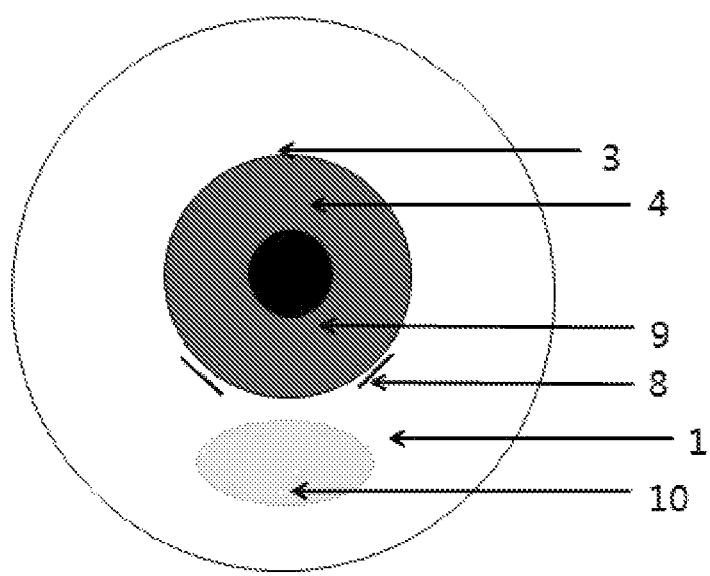
FIG. 6 is a schematic diagram showing a bulged filtering bleb and good formation of an anterior chamber after a surgery.

As shown in FIG. 1 in combination with FIGS. 2-8, a novel self-sealing trabeculectomy comprises the surgical steps:

S1: Before a surgery, disinfection, draping and eye speculum placement are conventionally conducted, an iodophor solution is diluted for irrigating a conjunctival sac, and local infiltration anesthesia is conducted under a surgical eye conjunctiva 1 with 0.4 ml of 2% lidocaine.

S2: Traction suturing 13 is conducted on a superior rectus 2 or a corneal limbus 3, then a superior corneoscleral limbus is fixed with suturing, a bulbar conjunctiva is annularly incised at an edge from a 11 o'clock position to a 1 o'clock position, and a conjunctival flap 4 is made with a corneoscleral limbus or a fornix as a base by taking the 12 o'clock position as a center.

S3: A 4 mm×3 mm or 4 mm×4 mm scleral flap 5 is made with a thickness of ½-⅔ of that of a sclera, and the scleral flap is used with or without an antimetabolite, wherein the 4 mm×3 mm or 4 mm×4 mm scleral flap is made using a diamond knife with scales; the scleral flap is in a step shape and is gradually thickened from the position away from the corneal limbus to the corneal limbus; and a thickness of the base of the scleral flap is necessary to be larger than ⅔ or above of the sclera.

S4: A root of an iris 6 (refer to FIG. 4) and trabecular tissues 7 (refer to FIG. 3) are conventionally resected, the scleral flap 5 is smoothed with a restoration instrument, and the bulbar conjunctiva is sutured with the nylon thread 8 to reach a watertight state, wherein the restoration instrument used is an iris restorer; and a 10-0 nylon thread is used for suturing the bulbar conjunctiva with 2 stitches, so as to achieve the watertight state. Of course, other restoration instruments may further be employed for restoring the iris.

Figure 7:
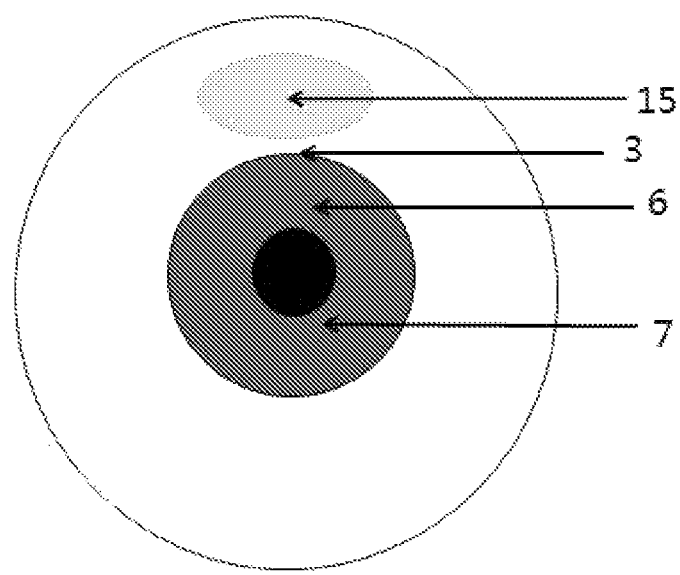
FIG. 7 is a schematic diagram showing a proper bulged filtering bleb and depth of an anterior chamber 3 months after a surgery.
Figure 8:
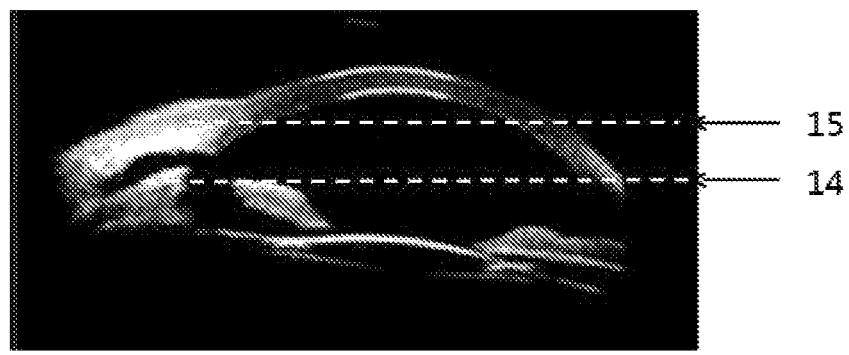
FIG. 8 is a schematic diagram of an unobstructed filtration channel shown under an ultrasound biomicroscope (UBM) 3 months after a surgery.

S5: A suspending suture for the rectus or a cornea is removed, the eye speculum is reduced to weaken a tension of the eye speculum, a patient is told to relax, and an anterior chamber 9 is formed 10 with normal saline or an anterior chamber irrigating solution, wherein if the anterior chamber is difficult to form, a conjunctival surface with the filtering bleb may be slightly pressed using the iris restorer, and the scleral flap is smoothed, so as to assist formation of the anterior chamber, referring to FIG. 6. FIG. 7 is a schematic diagram showing a proper bulged filtering bleb and depth of an anterior chamber 3 months after a surgery.

S6: The eye speculum is taken out, wherein for a part of patients still with poor formation of the anterior chambers, a filtering function adjusting device 11 is jointly placed in, and an antibiotic eye ointment is coated to finish the surgery. The filtering function adjusting device is a striped membrane made by silica gel, is in an approximate fan shape, has certain elasticity and plasticity and is closely adhered to the surface of the eyeball. The filtering function adjusting device is placed at an upper fornix 12, and a pressure is applied to the scleral flap by an own pressure and a force of an upper eyelid, so as to limit an outer filtering function of the scleral flap. Therefore, low intraocular pressure and a shallow anterior chamber in the early stage after the surgery are prevented, and the device plays a greater role after angle-closure glaucoma trabeculeclomy. The filtering function adjusting device may be removed or continuously worn at Day 3 after the surgery if necessary, and may be safely removed at Days 7-10 after the surgery generally.

S7: After the surgery, a corticosteroid hormone and a non-steroid anti-inflammatory drug are conventionally locally applied; if there is high intraocular pressure in an early stage after the surgery, an eyeball should not be massaged, and an anti-glaucoma drug may be additionally used first; if necessary, the edge of the scleral flap is slightly pressed at Day 3 after the surgery, and the fully closed scleral flap is gently opened; and at Day 7 after the surgery, normal eyeball massage is conducted to lower an intraocular pressure and keep a filtration channel unobstructed 14.

The Mechanism of the Surgery:

Due to the thick base of the scleral flap, the long scleral flap and the tension of coverage of the conjunctiva, the scleral flap may well keep slightly closed without affecting outflow of a small quantity of aqueous humor, and then the purpose of relative self closure is achieved. Implantation of the filtering function adjusting device may effectively prevent the low intraocular pressure and the shallow anterior chamber due to too strong filtration in the early stage after the surgery and improves the safety of the surgery. The filtering function adjusting device may be removed or continuously worn at Day 3 after the surgery if necessary. The filtering function adjusting device may be safely removed at Days 7-10 after the surgery generally.

Postsurgical Nursing Key Points:

After surgery, the corticosteroid hormone and the non-steroid anti-inflammatory drug are conventionally locally applied. If there is the high intraocular pressure in the early stage after the surgery, the eyeball should not be massaged, and the anti-glaucoma drug may be additionally used first. If necessary, at Day 3 after the surgery, the edge of the scleral flap may be slightly pressed, and the fully closed scleral flap is gently opened. At Day 7 after the surgery, normal eyeball massage may be conducted to lower the intraocular pressure and keep the filtration channel unobstructed.

Surgical Indications:

Various types of glaucoma requiring filtration surgeries. For a patient with angle-closure glaucoma, if there is poor formation of the anterior chamber after the surgery, a filtration pad temporary compression method may be employed outside the upper eyelid of the scleral flap if necessary, so as to reduce filtration and assist deepening of the anterior chamber.

The present invention has the beneficial effects that the self-sealing trabeculectomy breaks through the law of thinking that "the scleral flap requires to be sutured" of the trabeculectomy for the first time, achieves the characteristic of free suturing of the sclera through an improvement on the surgical technology and, compared with traditional trabeculectomy, has the following advantages that: 1. due to the self-sealing scleral flap, occurrence of postsurgical high and low intraocular pressure due to too tight and too loose sutures of the scleral flap is eliminated; and meanwhile, as the filtration channel of the scleral flap after the surgery is continuously unobstructed, the possibility of closure scars of the scleral flap is greatly lowered, and the success rate of the surgery is increased. 2. After the surgery, the steps of laser suture lysis, adjusting suture removal and the like are not required, so that pain of the patient is reduced, and the maintenance process for the filtering bleb after the surgery is simplified. 3. Without stimulation with the suture under the scleral flap, scarring of the scleral flap after the trabeculectomy is further lowered, and the success rate of an anti-glaucoma surgery is increased. 4. Surgically induced astigmatism caused by looseness and tightness of the sclera suture after the surgery is reduced or eliminated, and the visual quality of the patient after the surgery is improved. 5. The surgical steps are simplified, the surgery time is shortened, and the tolerance and postsurgical recovery of the patient are more facilitated. 6. In combination with the trabecula filtering function adjusting device, occurrence of too strong early filtration after the surgery may be avoided, and then the safety of the surgery is greatly improved.

In description of the present invention, it should be noted that orientations or positional relationships indicated by terms "longitudinal", "horizontal", "upper", "lower", "front", "rear", "left", "right", "vertical", "horizontal", "top", "bottom", "inner", "outer" and the like are based on orientations or positional relationships shown in the drawings, are to facilitate the description of the present invention and simplify the description merely, do not indicate or imply that the referred apparatuses or elements must have specific orientations and are constructed and operated in the specific orientations and thus should not be construed to limit the present invention. Moreover, terms like "first" and "second" are only used for description, not be considered as a designation or designation of relative importance.

In description of the present invention, it should be noted that unless otherwise expressly specified and defined, the terms "mounted", "connected" and "coupled" should be understood broadly, for example, as fixed connection, detachable connection or integral connection; mechanical connection or electrical connection; and direct connection, indirect connection through an intermediary medium or communicating between interiors of two elements. The meanings of above terms in the present invention may be understood in specific cases to those skilled in the art. In addition, in the description of the present invention, "a plurality" means two or more, unless otherwise specifically defined.

Notices for the skilled persons: although the present invention has made descriptions according to the above specific implementations, the idea of the present invention is not limited to the present invention, and any modification applying the idea of the present invention will be within the protection scope of the patent right of the present invention.

The invention claimed is:

1. A self-sealing trabeculectomy, comprising the surgical steps of:
   S1: before a surgery, conventionally conducting disinfection, draping and eye speculum placement, diluting an iodophor solution for irrigating a conjunctival sac, and conducting local infiltration anesthesia under a surgical eye conjunctiva (1) with 0.4 ml of 2% lidocaine;
   S2: conducting traction suturing (13) on a superior rectus (2) or a corneal limbus (3), then fixing a superior corneoscleral limbus with suturing, annularly incising a bulbar conjunctiva at an edge from a 11 o'clock position to a 1 o'clock position, and making a conjunctival flap (4) with a corneoscleral limbus or a fornix as a base by taking 12 o'clock position as a center;
   S3: making a 4 mm×3 mm or 4 mm×4 mm scleral flap (5) with a thickness of ½-⅔ of that of a sclera, and using the scleral flap (5) with or without an antimetabolite;
   S4: resecting a root of an iris (6) and trabecular tissues (7), smoothing the scleral flap (5) with a restoration instrument, and suturing the bulbar conjunctiva with a nylon thread (8) to reach a watertight state;
   S5: removing a suspending suture of the traction suturing (13) of S2 for the rectus or a cornea, reducing the eye speculum to weaken a tension of the eye speculum, and forming an anterior chamber (9) with normal saline or an anterior chamber (9) irrigating solution;
   S6: taking out the eye speculum; and
   S7: after the surgery, locally applying a corticosteroid hormone and a non-steroid anti-inflammatory drug; if there is high intraocular pressure in an early stage after the surgery, not massaging an eyeball, and additionally using an anti-glaucoma drug first; if necessary, slightly pressing the edge of the scleral flap (5) at Day 3 after the surgery, and gently opening the fully closed scleral flap (5); and at Day 7 after the surgery, conducting normal eyeball massage to lower an intraocular pressure and keep a filtration channel unobstructed (14).

2. The self-sealing trabeculectomy according to claim 1, wherein in step S3, the 4 mm×3 mm or 4 mm×4 mm scleral flap (5) is made using a diamond knife with scales.

3. The self-sealing trabeculectomy according to claim 1, wherein in step S3, the scleral flap (5) is in a step shape and is gradually thickened from the position away from the corneal limbus to the corneal limbus; and a thickness of the base of the scleral flap (5) is necessary to be larger than ⅔ or above of a sclera.

4. The self-sealing trabeculectomy according to claim 1, wherein in step S4, the restoration instrument used is an iris restorer; and a 10-0 nylon thread is used for suturing the bulbar conjunctiva with 2 stitches, to achieve the watertight state.

5. The self-sealing trabeculectomy according to claim 1, wherein in step S5, if the anterior chamber (9) is difficult to form, a conjunctival surface (10) with the filtering bleb may be slightly pressed using the iris restorer, and the scleral flap (5) is smoothed, to assist formation of the anterior chamber (9).

6. The self-sealing trabeculectomy according to claim 1, wherein in step S6, for a part of patients still with poor formation of the anterior chambers, a filtering function adjusting device (11) is jointly placed in, and an antibiotic eye ointment is coated to finish the surgery.

7. The self-sealing trabeculectomy according to claim 6, wherein the filtering function adjusting device (11) is a striped membrane made by silica gel, is in an approximate fan shape, has certain elasticity and plasticity and is closely adhered to the surface of the eyeball.

8. The self-sealing trabeculectomy according to claim 6, wherein the filtering function adjusting device (11) is placed at an upper fornix (12), and a pressure is applied to the scleral flap (5) by an own pressure and a force of an upper eyelid, to limit an outer filtering function of the scleral flap (5).

9. The self-sealing trabeculectomy according to claim 6, wherein the filtering function adjusting device (11) may be removed or continuously worn at Day 3 after the surgery if necessary, and may be safely removed at Days 7-10 after the surgery generally.

* * * * *